United States Patent [19]

Senuma et al.

[11] 4,175,206
[45] Nov. 20, 1979

[54] PROCESS FOR PREPARING A HYDROXYPHENYLGLYCINE COMPOUND

[75] Inventors: Masaru Senuma, Takatsuki; Nobuhiko Ishihara, Neyagawa; Shigeru Nishimoto, Minoo; Eisaku Yamato, Kobe; Noboru Shigematsu, Nishinomiya, all of Japan

[73] Assignee: Tanabe Seiyaku Co., Ltd., Osaka, Japan

[21] Appl. No.: 903,492

[22] Filed: May 8, 1978

[51] Int. Cl.² .................................................. C07C 51/00
[52] U.S. Cl. .................................................. 562/444
[58] Field of Search .......................... 560/39; 562/444

[56] References Cited

FOREIGN PATENT DOCUMENTS 1353612  5/1974  United Kingdom ...................... 562/442
1371896 10/1974  United Kingdom ...................... 562/442

OTHER PUBLICATIONS

Morrison et al., Organic Chemistry, pp. 64–111 (1966).

Primary Examiner—James H. Reamer
Attorney, Agent, or Firm—Bierman & Bierman

[57] ABSTRACT

Glyoxylic acid or a salt of glyoxylic, an ammonium salt of an organic or inorganic acid and a phenol compound of the formula:

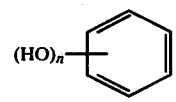

wherein n is an integer of one to three, are condensed together to prepare hydroxyphenylglycine compounds of the formula:

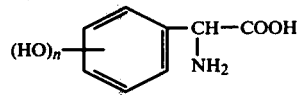

wherein n is the same as defined above. The hydroxyphenylglycine compounds thus obtained are useful as intermediates in the synthesis of penicillins and cephalosporins.

2 Claims, No Drawings

PROCESS FOR PREPARING A HYDROXYPHENYLGLYCINE COMPOUND

BACKGROUND OF INVENTION

This invention relates to a novel process for preparing hydroxyphenylglycine compounds of the formula:

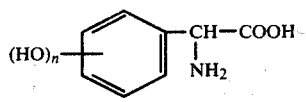
(I)

wherein n is an integer of one to three.

Hydroxyphenylglycine compounds (I) of the invention are useful as intermediates in the synthesis of penicillins and cephalosporins.

It is known that hydroxyphenylglycine compounds may be prepared by condensation of a hydroxybenzaldehyde, sodium cyanide and ammonium bicarbonate to give the corresponding hydroxybenzylhydantoin. This procedure is followed by hydrolysis with sodium hydroxide. It is also known that hydroxyphenylglycine compounds may be obtained by the Strecker synthesis (i.e., condensing a hydroxybenzaldehyde and ammonium cyanide, and then hydrolyzing the resultant hydroxybenzylaminonitrile with hydrochloric acid). However, the hydroxybenzaldehyde employed as one of the starting materials therein is too expensive for practical use in large scale production of hydroxyphenyglycine compounds. In addition, since the hydrolysis step of these known methods are conducted at a high temperature such as 100° to 120° C. for a long period of time (e.g., 4 to 40 hours), the intermediate and final products thereof tend to cause partial decomposition during the hydrolysis step if the hydroxy group thereof has not been protected beforehand.

In addition to the above-mentioned methods, British Pat. Nos. 1353612 and 1371896 disclose the preparation of hydroxyphenylglcine compounds by condensing glyoxylic acid with ammonia and phenol. However, since this method is usually carried out under alkaline conditions by using an excess amount of concentrated ammonia and phenol, undesirable resinous products are obtained during the reaction and additional steps are required to remove the resulting contaminants. Moreover, this method results in the formation of an ammonium salt of hydroxyglycine [HOCH2(NH2)COONH4-] and the condensation product (i.e., the hydroxyphenylglycine compound) is always obtained in the form of a water-soluble ammonium salt. Therefore, the isolation and recovery of the highly pure hydroxyphenylglycine compound as the free acid is only possible by resorting to the costly and time consuming steps of (1) extracting excess phenol with a solvent; (2) distilling the reaction solution to remove ammonia; (3) neutralizing the reaction solution with concentrated hydrochloric acid; and (4) again neutralizing the resultant hydrochloride with ammonia to liberate the free hydroxyphenylglycine compound.

As a result of our investigations we have discovered a novel method for the production of hydroxyphenylglycine compounds. This method results in the precipitation of crystals of the free acid form of the hydroxyphenylglycine compounds as the reaction proceeds. Thus, highly pure hydroxyphenylglycine compounds can be readily recovered by simply filtrating the reaction solution.

This method is accomplished by condensing glyoxylic acid or one of the salts of glyoxylic acid and phenol and an ammonium salt of an organic or inorganic acid under neutral or acidic conditions. Thus, an object of the present invention is to provide a practical and economical process for the industrial scale production of hydroxyphenylglycine compounds. Another object of the invention is to provide a method which makes it possible to prepare highly pure free hydroxyphenylglycine compounds without purification techniques required in prior art methods. Another object is to provide a method of preparing said compounds without using an excess of concentrated ammonia. Additional objects of the present invention will be clearly observed from the following description.

SUMMARY OF INVENTION

According to the present invention, hydroxyphenylglycine compounds (I) can be prepared by reacting a phenol compound of the formula:

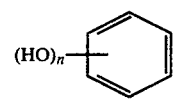
(II)

wherein n is the same as defined above, with glyoxylic acid or one of the salts of glyoxylic acid and an ammonium salt of a water-soluble organic or inorganic acid.

Suitable examples of the glyoxylic acid salt include ammonium salt, alkali metal salts (e.g., sodium and potassium salts) and the like. Additionally, phenol, catechol, resorcinol, pyrogallol and the like are suitably employed as the phenol compound (II) of the present invention. Moreover, examples of the ammonium salt of the water-soluble organic or inorganic acid which are employed include the salts of an alkanoic acid having one to three carbon atoms such as ammonium acetate, ammonium formate or ammonium propionate; the salts of an organic dicarboxylic acid having three to five carbon atoms such as ammonium tartrate; and inorganic acid salts such as ammonium carbonate, ammonium bicarbonate, ammonium thiocyanate, ammonium chloride, ammonium sulfate, ammonium primary phosphate [(NH4)2HPO4] or ammonium secondary phosphate [(NH4)H2PO4].

Among these various ammonium salts, the most preferred examples thereof include an ammonium salt of an alkanoic acid having one to three carbon atoms. Other preferred examples of said ammonium salt include an inorganic acid salt selected from the group consisting of ammonium carbonate, ammonium bicarbonate, ammonium thiocyanate, ammonium chloride, ammonium sulfate and ammonium secondary phosphate.

Preferably, the phenol compound (II) is used in an amount of between about one and 2 moles per mole of glyoxylic acid (or its salts), and the ammonium salt of the organic or inorganic acid in an amount of between about one and 5 moles, especially about 3 moles, per mole of said glyoxylic acid (or its salts).

The condensation reaction of the present invention can be readily accomplished in an aqueous solvent. It is preferred to carry the reaction out at a temperature of between about 10° C. and 60° C., especially between about 20° C. and 40° C. Water and a mixture of water and an alkanol of one to three carbon atoms (e.g., aqueous methanol and aqueous ethanol) are suitable as the reaction solvent.

The reaction can be suitably carried out without adjusting the pH of the reaction solution, i.e., under approximately neutral conditions. Additionally, the reaction of the present invention may be preferably carried out by adding all of the starting materials (i.e. glyoxylic acid or one of its salts, the phenol compound and the ammonium salt of the organic or inorganic acid) to the solvent at the same time. When the reaction is completed as above, the hydroxyphenylglycine compounds (I) in the free acid form are always obtained as crystalline precipitates and can be readily recovered in highly pure form by simply filtering or centrifuging the reaction solution.

DESCRIPTION OF PREFERRED EMBODIMENTS

Practical and presently-preferred embodiments of the present invention shown in the following examples. These embodiments are for illustrative purposes only and are not meant to limit or in anyway redefine the invention as claimed in the broadest claim of the present application.

EXAMPLE 1

36.9 g of sodium glyoxylate are added to 130 ml of water, and 75 g of ammonium acetate and 60 g of phenol are added thereto under stirring. The mixture is stirred at 30° to 35° C. for 48 hours. After the reaction, the crystalline precipitates are collected by filtration under cooling, and then successively washed with water and methanol. 27.2 g of DL-p-hydroxyphenylglycine are thereby obtained as white crystals.

Yield: 50.4%, M.P. 225°–228° C. (decomp.), Purity: 98.5%.

EXAMPLE 2

42.1 g of potassium glyoxylate, 75 g of ammonium acetate, 60 g of phenol and 130 ml of water are treated in the same manner as described in Example 1. The reaction was conducted for a period of 24 hours. 18.1 g of DL-p-hydroxyphenylglycine are thereby obtained as crystals. Yield 33.6%.

EXAMPLE 3

30 g of an aqueous 40% glyoxylic acid solution are added to 70 ml of water, and 37.5 g of ammonium acetate and 22.5 g of phenol are added thereto under stirring. The mixture is stirred at room temperature for 41 hours. The crystalline precipitates are collected by filtration under cooling, and then successively washed with water and methanol. 7.8 g of DL-p-hydroxyphenylglycine are thereby obtained as white crystals. Yield: 28.9%, M.p. 225°–228° C. (decomp.).

EXAMPLE 4

29.5 g of ammonium glyoxylate, 75 g of ammonium acetate, 60 g of phenol and 130 ml of water are treated in the same manner as described in Example 1. 21.9 g of DL-p-hydroxyphenylglycine are thereby obtained as crystals. Yield: 40.5%, M.p. 225°–228° C. (decomp.).

DL-p-hydroxyphenylglycine (purity: 97.8%) is obtained in a yield of 52.3% by carrying out the above-mentioned reaction at 20° to 25° C. for 120 hours.

EXAMPLE 5

36.9 g of sodium glyoxylate, 61.3 g of ammonium formate, 60 g of phenol and 130 g of water are treated in the same manner as described in Example 1. 18.5 g of DL-p-hydroxyphenylglycine are thereby obtained as crystals. Yield: 34.2% M.p. 225°–228° C. (decomp.).

EXAMPLE 6

36.9 g of sodium glyoxylate, 75 g of ammonium acetate, 72 g of catechol and 130 ml of water are treated in the same manner as described in Example 1. 11.0 g of DL-(3,4-dihydroxyphenyl)glycine are thereby obtained as crystals. Yield: 18.5 g M.p. 185°–188° C. (decomp.).

EXAMPLE 7

36.9 g of sodium glyoxylate, 75 g of ammonium acetate, 81.5 g of pyrogallol and 130 ml of water are treated in the same manner as described in Example 1. 13.3 g of DL-(2,3,4-trihydroxyphenyl)glycine are thereby obtained as crystals. Yield: 20.6% M.p. 198°–203° C. (decomp.).

EXAMPLE 8

Resorcinol is employed instead of phenol in Example 1, whereby DL-(2,4-dihydroxyphenyl)glycine is obtained.

EXAMPLE 9

64 g of ammonium sulfate are employed instead of the ammonium acetate used in Example 1. 14.7 g of DL p-hydroxyphenylglycine are thereby obtained as crystals. M.p. 225°–228° C. (decomp.), Yield 27.5%.

EXAMPLE 10

74 g of ammonium thiocyanate are employed instead of the ammonium acetate used in Example 1. 13.7 g of DL-p-hydroxyphenylglycine are thereby obtained as crystals. Yield: 25.3%, M.p. 225°–228° C. (decomp.).

EXAMPLE 11

77 g of ammonium bicarbonate are employed instead of the ammonium acetate used in Example 1. 18.2 g of DL-p-hydroxyphenylglycine are thereby obtained as crystals. Yield: 33.7%, M.p. 225°–228° C. (decomp.).

EXAMPLE 12

64 g of ammonium secondary phosphate [$(NH_4)H_2PO_4$] are employed instead of the ammonium acetate used in Example 1. 13.0 g of DL-p-hydroxyphenylglycine are thereby obtained as crystals. Yield: 24.0%, M.p. 225°–228° C. (decomp.).

EXAMPLE 13

52 g of ammonium chloride are employed instead of the ammonium acetate used in Example 1. 16.6 g of DL-p-hydroxyphenylglycine are thereby obtained as crystals. Yield: 30.8%, M.p. 225°–228° C. (decomp.).

What we claim is:

1. A process for preparing DL-hydroxyphenylglycine which comprises reacting phenol with a first compound selected from glyoxylic acid, ammonium glyoxidate, sodium glyoxidate, and potassium glyoxidate, and a second compound selected from ammonium alkanoate having one to three carbon atoms.

2. The process according to claim 1, where said first compound is reacted with between about one and two moles of phenol per mole of said first compound and between about one to five moles of said second compound per mole of said first compound at a temperature of between about 10° C. and 60° C. in an aqueous solvent.

* * * * *

UNITED STATES PATENT AND TRADEMARK OFFICE
CERTIFICATE OF CORRECTION

PATENT NO. : 4,175,206

DATED : November 20, 1979

INVENTOR(S) : Masaru Senuma, Nobuhiko Ishihara, Shigeru Nishimoto, Eisaku Yamato, and Noboru Shigematsu It is certified that error appears in the above-identified patent and that said Letters Patent are hereby corrected as shown below:

In Claim 1, lines 3 - 4, cancel "glyoxidate" (all occurrences) and substitute therefor --glyoxylate--.

Signed and Sealed this

Twenty-fifth Day of March 1980

[SEAL]

Attest:

SIDNEY A. DIAMOND

Attesting Officer

Commissioner of Patents and Trademarks